United States Patent [19]

Köhler

[11] Patent Number: 5,436,365
[45] Date of Patent: Jul. 25, 1995

[54] PROCESS FOR THE PREPARATION OF PIMELIC ESTERS

[75] Inventor: Günther Köhler, Marl, Germany

[73] Assignee: Huels Aktiengesellschaft, Marl, Germany

[21] Appl. No.: 302,971

[22] Filed: Sep. 12, 1994

[30] Foreign Application Priority Data

Sep. 13, 1993 [DE] Germany .................. 43 31 000.1

[51] Int. Cl.6 ............................................. C07C 67/00
[52] U.S. Cl. .................................................. 560/204
[58] Field of Search ....................................... 560/204

[56] References Cited

PUBLICATIONS

Chem Abstracts 83:205804a 1975.
Chem Abstracts On Line Printout 83:192492; 1975.
Chem Abstracts On Line Printout 120:163605; 1993.

Primary Examiner—José G. Dees
Assistant Examiner—Samuel Barts
Attorney, Agent, or Firm—Oblon, Spivak, McClelland, Maier & Neustadt

[57] ABSTRACT

A method is provided for the preparation of a pimelic ester of the formula:

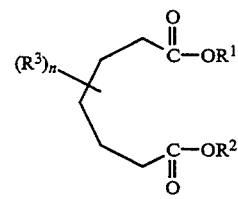

wherein $R^1$ and $R^2$ may be identical or different, and are linear or branched saturated alkyl substituents having from 1 to 10 carbons or araliphatic radicals having 7 to 10 carbon atoms; $R^3$ is H or a hydrocarbon radical of one to six carbon atoms, and n is an integer of from 0 to 3; wherein the method entails:

reacting a salt, formed from reaction of a 2-oxocyclohexanecarboxylic ester with a strong base, with an alcohol at a temperature of 50°–250° C., to cause ring opening.

15 Claims, No Drawings

PROCESS FOR THE PREPARATION OF PIMELIC ESTERS

BACKGROUND OF THE INVENTION

1. Field of the Invention

The present invention relates to a new process for the preparation of pimelic esters, by a ring-opening reaction of a salt formed from a 2-oxocyclohexanecarboxylic ester and a strong base.

2. Discussion of the Background

Pimelic esters, as defined in the present application, have the following formula:

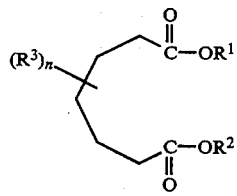

wherein $R^1$ and $R^2$ may be identical or different, and are linear or branched saturated alkyl substituents having from 1 to 10 carbons or araliphatic radicals having 7 to 10 carbon atoms; $R^3$ is H or a hydrocarbon radical of one to six carbon atoms, and n is an integer of from 0 to 3. Pimelic esters are important intermediates in the preparation of pharmaceuticals, crop protection agents, perfumes or cosmetic active substances, specialty polymers and lubricants.

Pimelic acid has been prepared by a number of different synthetic routes. It is known that pimelic acid can be prepared by partial hydrogenation of salicylic acid—to give tetrahydrosalicylic acid—with subsequent cleavage by sodium hydroxide or potassium hydroxide under drastic conditions; cf. *Ullmann*, Volume 5, p. 824 (19.54) and Volume 10, p. 140 (1980) and *Org. Synthesis Coll. II*, pp. 531–38 (1943). Pimelic acid can also be obtained by alkali treatment of cyclohex-4-enecarboxylic acid, which itself can be obtained from butadiene and acrylic acid by a Dieis-Alder reaction [*J. Amer. Chem. Soc.* 74, p. 532 (1952)].

Pimelic acid can also be prepared by reaction of alkali metal or alkali metal hydroxides with tetrahydrobenzaldehyde in accordance with German Patent 7331 or with tetrahydrofurylpropanol in accordance with German Patent 2939.

According to the process of EP-A 0 905 651, the synthesis can also be carried out by reduction of 3-oxopimelic ester.

Other synthesis routes start from suberone, which is converted to pimelic acid by oxidative cleavage; cf. U.S. Pat. No. 286,516 and DE-A 20 43 012. The same result is obtained by hydrolysing cyclohexanone-2-carboxamide; cf. DD Patent 112 987.

Pimelic acid is also the result of the oxidation of cycloalkenes with ozone in accordance with DE-A 40 00 163, the hydroformylation of 1,5-pentadiene followed by oxidation in accordance with DE-A 15 18 216, or the carbonylation of ω-caprolactone in accordance with U.S. Pat. No. 4,888,443.

However, for many applications it is the esters of pimelic acid which are desired, which have to be prepared from pimelic acid, after the syntheses described above, by esterification according to known methods. These syntheses, which often involve two or more stages, and the subsequent esterification to obtain pimelic esters are highly complex. In addition, none of the known processes provide satisfactory yields and purity combined with ease of manufacture.

SUMMARY OF THE INVENTION

Accordingly, one object of the present invention is to provide a method for preparing pimelic esters which provides high yields and purity while using a minimal number of steps in the synthesis.

A further object of the present invention is to provide a method for preparing pimelic esters which does not require the isolation and/or purification of intermediate products along the synthesis path.

These and other objects of the present invention have been satisfied by the discovery of a method for preparing pimelic esters which comprises by reacting salts of 2-oxocyclohexanecarboxylic esters and strong organic bases with alcohols at elevated temperatures, to cause ring opening, forming the dialkyl pimelates directly with high selectivity and yield.

DETAILED DESCRIPTION OF THE PREFERRED EMBODIMENTS

The present invention relates to a method for the preparation of a pimelic ester of the formula:

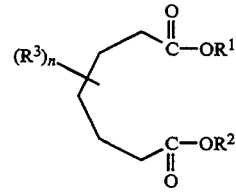

wherein $R^1$ and $R^2$ may be identical or different, and are linear or branched saturated alkyl substituents having from 1 to 10 carbons or araliphatic radicals having 7 to 10 carbon atoms; $R^3$ is H or a hydrocarbon radical of one to six carbon atoms, and n is an integer of from 0 to 3; comprising:

reacting a salt, formed from reaction of a 2-oxocyclohexanecarboxylic ester with a strong base, with an alcohol at a temperature of 50°–250° C., to cause ring opening.

In comparison with known processes, a further embodiment of the method according to the present invention provides a simple, economic and direct route to dialkyl esters of pimelic acid in accordance with Equations I and II.

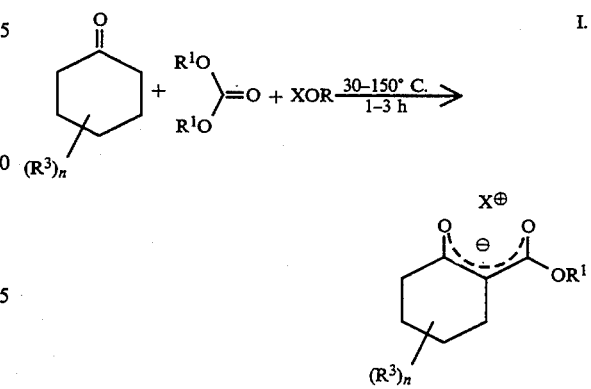

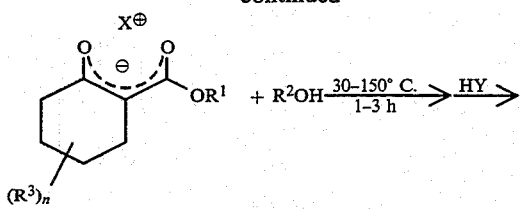

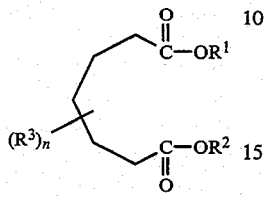

It is surprising, and was not known previously, that a salt of a strong base with the acidic β-keto ester compound of cyclohexanone, the intermediate in this synthesis, is usually not isolated and may preferably be the salt of an alkali metal, for example Na or K, is cleaved with an alcohol to give the pimelic esters.

The method of the present invention provides for the ring opening of a 2-oxocyclohexanecarboxylic ester salt by reaction with an alcohol at elevated temperature.

The process of the present invention optionally includes the preparation of the 2-oxocyclohexanecarboxylic ester by conventional carboxylation of cyclohexanone, which is optionally substituted by alkyl. At the same time or subsequently to the carboxylation of cyclohexanone, the corresponding salt is formed in the presence of a strong base and is subjected to a ring-opening reaction with an alcohol at temperatures of 50°–250° C., thus forming the pimelic ester.

The synthesis of the 2-oxocyclohexanecarboxylic esters (Equation I) is carried out by conventional methods, such as by carboxylating the known and favorably priced starting material cyclohexanone with a dialkyl carbonate in the presence of alkali metal alkoxide or aryloxide bases. The reaction may be performed neat or with a solvent, but it is preferable to employ a solvent, in order to ensure that the reaction mixture remains in a readily stirrable condition. Examples of suitable solvents include toluene, cyclohexane, tert-butyl methyl ether, xylene, mesitylene, tert-butylbenzene, p-tert-butyltoluene, and also polar solvents such as anisole, alkylanisole, phenoxyethanol, diglyme, benzyl alcohol, or 3,3,5-trimethylcyclohexanone. Further, it is possible to use the dialkyl carbonate as both a reactant and a solvent as long as the dialkyl carbonate will dissolve the reaction mixture. Suitable dialkyl carbonates for use as both a reactant and a solvent include dimethyl carbonate and diethyl carbonate.

The reaction of the present invention in accordance with Equation II takes place only when the reaction of Equation I has finished, or can only be initiated once the salt of an oxocyclohexanecarboxylic ester with a strong base has been formed.

If lower alcohols are used, for example methanol, ethanol or propanol, the reaction can also take place at atmospheric pressure under reflux. It is more preferred to perform the ring opening at an elevated temperature of from 90° C. to 250° C. over the course of from 10 to 30 minutes under pressure which is slightly elevated to provide an acceptable rate of reflux without flashing the alcohol or solvent at the elevated temperatures. When higher alcohols are used whose boiling points are above 90° C., this procedure can also be carried out under atmospheric pressure and under reflux.

As an alternative embodiment, the ring opening of Equation II can also be performed using lower alcohols, such as methanol, ethanol or propanol, at higher temperatures, for example 120° C., and under atmospheric pressure. However, in order to do so, the lower alcohol must be metered in at a slow rate such that ring opening takes place, consuming the alcohol, immediately upon its addition.

If the treatment of the 2-oxocyclohexanecarboxylic ester takes place with an alcohol different to or higher boiling than that of the alcohol residue in the 2-oxocyclohexanecarboxylic ester, then mixed pimelic esters are formed. With an excess of base and a longer reaction time, however, it is also possible for the symmetric diester of the higher boiling alcohol to be formed if the lower-boiling alcohol is removed during the reaction.

1–20 equivalents of alcohol are employed per equivalent of 2-oxocyclohexanecarboxylic ester or salt thereof. The base used is preferably the solid alkali metal alcoholate of the alcohol to be employed, or its alcoholic solution, in a quantity of 1—3 equivalents per equivalent of 2-oxocyclohexanecarboxylic acid.

The reactions according to Equations I and II can be carried out in succession in one reaction vessel, in a semi-batchwise procedure, or alternatively can be carried out in semi-continuous operation. One advantage provided by the present process is that there is no need to isolate the intermediate product formed by carboxylation of the cyclohexanone. However, such isolation can be performed if desired.

A conventional acidic work up is used to isolate the pimelic ester formed. The acid used may be a mineral acid such as HCl, $H_2SO_4$, $HNO_3$ or $H_3PO_4$, an organic acid, such as formic acid, acetic acid, propionic acid or butyric acid or a fatty acid, such as 2-ethylhexanoic acid.

After the acidic work-up, the resulting pimelic ester can be readily obtained by distillation from the working mixture.

Other features of the present invention will become apparent in the course of the following descriptions of specific examples, which are provided herein merely for illustrative purposes and are not intended to be limiting of the invention unless otherwise indicated.

EXAMPLES

Example 1

236 g (2 mol) of diethyl carbonate and 136 g (2 mol) of sodium ethoxide in powder form together with 200 g of toluene were placed in a 1 l stirred flask at room temperature and heated to 40° C. 147 g (1.5 mol) of cyclohexanone were metered in over the course of 2 h. 92 g (2 mol) of ethanol were then added and the mixture was boiled at reflux for 12 h. Subsequently, 500 ml of 10% strength $H_2SO_4$ were run in, resulting in the formation of two phases which were easily separated from one another. The aqueous phase was extracted with a small portion of toluene. The organic phases were combined and distilled.

The main product was 282 g of diethyl pimelate (b.p. 178° C./40 mbar), corresponding to a yield of 87%. Unreacted diethyl carbonate and toluene can be recycled.

Example 2

180 g (2 mol) of dimethyl carbonate and 108 g (2 mol) of sodium methoxide in powder form together with 200 g of toluene were brought together at room temperature. 137 g (1.4 mol) of cyclohexanone were metered into this mixture at 40° C. over the course of 2 h. 96 g (3 mol) of methanol were then added. This mixture was stirred at 110° C. for 1 h in a pressure vessel (at approximately 3 bar).

For working up, 500 ml of 10% strength $H_3PO_4$ were added. After phase separation and extraction of the aqueous phase using 100 ml of toluene, the organic phases were combined and distilled. The main product was 224 g of dimethyl pimelate (b.p. 134° C./20 mbar), a yield of 85%.

Example 3

236 g (2 mol) of diethyl carbonate, 136 g (2 mol) of sodium ethoxide in powder form and 200 g of anisole were placed in a glass flask equipped with a reflux condenser and stirrer. 147 g (1.5 mol) of cyclohexanone were metered in at 40° C. over the course of 3 h. Following this reaction period, 148 g (2 mol) of 1-butanol were added. The mixture was then heated to 120° C., at which reflux ensued. After 1 h the mixture was cooled and worked up with 500 ml of 10% strength $H_3PO_4$. The organic phase was distilled in vacuo. The main product was 285 g of butyl ethyl pimelate (b.p. 178° C./25 mbar), corresponding to a yield of 78%.

Example 4

270 g (3 mol) of dimethyl carbonate, 162 g (3 mol) of sodium methoxide in powder form and 300 g of 4-tert-butyltoluene were placed in a 2 1 glass flask equipped with a stirrer. 231 g (1.5 mol) of 4-tert-butylcyclohexanone were metered in at 50° C. over the course of 3 h. Subsequently the mixture was heated at 120° C. in a pressure vessel with 300 g of methanol and was stirred for 1 h.

500 ml of 10% strength $H_2SO_4$ were then added. Two phases formed, which were easily separated. The aqueous phase was extracted with 4-tert-butyltoluene. The combined organic phases were then distilled, the main fraction containing 244 g of dimethyl 4-tert-butylpimelate (86% yield).

Example 5

180 g (2 mol) of dimethyl carbonate, 330 g (2 mol) of 30% strength sodium methoxide solution, 200 g of anisole and 180 g of 1-butanol were placed in a glass flask equipped with a stirrer. The mixture was boiled at reflux for 3 h. The excess methanol was then removed by distillation. After a transesterification of the dimethyl to the dibutyl carbonate was essentially complete, 147 g (1.5 mol) of cyclohexanone were metered in at 70° C. over the course of 2 h. After this a further 200 g of 1-butanol were added and the mixture was boiled at reflux at about 120° C. to provide, after work up, di-n-butyl pimelate.

Example 6

348 g (2 mol) of di-n-butyl carbonate and 140 g (2 mol) of potassium methoxide powder were placed together with 500 ml of 4-tert-butyltoluene in a reaction vessel equipped with a stirrer. 154 g (1 mol) of 4-tert-butylcyclohexanone were metered in at 40° C. over the course of 4 h. The mixture was subsequently stirred with 400 g of n-butanol at 110° C. for 3 h. 600 ml of 10% strength HCl were then added, forming two phases which were easily separated. The aqueous phase was extracted several times with 4-tert-butyl toluene. The combined organic phases were distilled to give 180 g of dibutyl 4-tert-butylpimelate, corresponding to a yield of 74%.

Obviously, numerous modifications and variations of the present invention are possible in light of the teachings above. It is therefore to be understood that within the scope of the appended claims, the invention may be practiced otherwise than as specifically described herein.

What is claimed as new and is desired to be secured by Letters Patent of the United States is:

1. A method for the preparation of a pimelic ester of the formula:

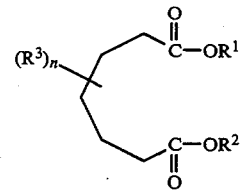

wherein $R^1$ and $R2$ may be identical or different, and are linear or branched saturated alkyl substituents having from 1 to 10 carbons or araliphatic radicals having 7 to 10 carbon atoms; $R^3$ is H or a hydrocarbon radical of one to six carbon atoms, and n is an integer of from 0 to 3; wherein the method comprises:
  forming a salt of 2-oxocyclohexanecarboxylic ester by reaction of cyclohexanone with a dialkyl carbonate in the presence of a strong base, wherein the salt is not isolated before further reaction, and
  reacting said salt with an alcohol at a temperature of 90°–250° C., to cause ring opening.

2. The method according to claim 1, wherein said alcohol is a member selected from the group consisting of branched and unbranched aliphatic alcohols having 1 to 10 carbon atoms, and araliphatic alcohols having 7 to 12 carbon atoms.

3. The method according to claim 2, wherein said alcohol is a member selected from the group consisting of branched and unbranched aliphatic alcohols having from 1 to 3 carbon atoms.

4. The method according to claim 1, wherein said alcohol is present in an amount of from 1 to 20 equivalents of alcohol per equivalent of 2-oxocyclohexanecarboxylic ester or salts thereof.

5. The method according to claim 1, wherein said strong base is an alkali metal alcoholate, in a quantity of 1 to 3 equivalents per equivalent of 2-oxocyclohexanecarboxylic ester.

6. The method according to claim 5, wherein said alkali metal alcoholate is an alkali metal alcoholate prepared from the alcohol used to effect ring opening.

7. The method according to claim 1, wherein said reacting step is carried out under sufficient pressure to maintain reaction at a temperature above an atmospheric boiling point of the alcohol.

8. The method according to claim 1, wherein said strong base is added over the course of the reaction.

9. The method according to claim 8, wherein said strong base is added in portions over the course of the reaction.

10. The method according to claim 8, wherein said strong base is added continuously over the course of the reaction.

11. The method according to claim 8, wherein said strong base is added as a solid.

12. The method according to claim 8, wherein said strong base is an alkali metal alcoholate and is added as an alcoholic solution of the alkali metal alcoholate.

13. The method according to claim 1, wherein said strong base is an alkali metal alcoholate.

14. The method according to claim 1, wherein said reacting step is carried out in the presence of a solvent, selected from the group consisting of aromatic, aliphatic and alicyclic hydrocarbons, aliphatic and aromatically substituted ethers, fatty alcohols and cyclic carbonates.

15. The method according to claim 1, wherein said reacting step is performed at atmospheric pressure and at a temperature above an atmospheric boiling point of the alcohol by adding the alcohol slowly over the course of the reaction, such that the alcohol is consumed by the reaction immediately upon addition to the reaction.

* * * * *